(12) United States Patent
Broz

(10) Patent No.: US 10,278,871 B2
(45) Date of Patent: May 7, 2019

(54) ABG STRETCH TAPE

(71) Applicant: John Broz, Las Vegas, NV (US)

(72) Inventor: John Broz, Las Vegas, NV (US)

(73) Assignee: John Broz, Las Vegas, NV (US)

(*) Notice: Subject to any disclaimer, the term of this patent is extended or adjusted under 35 U.S.C. 154(b) by 0 days.

(21) Appl. No.: 15/278,957

(22) Filed: Sep. 28, 2016

(65) Prior Publication Data

US 2018/0086947 A1    Mar. 29, 2018

(51) Int. Cl.
| | | |
|---|---|---|
| *A61F 13/02* | (2006.01) |
| *A61F 13/08* | (2006.01) |
| *A61F 13/00* | (2006.01) |
| *A61F 13/10* | (2006.01) |
| *A61L 24/04* | (2006.01) |
| *C09J 7/21* | (2018.01) |
| *C09J 201/00* | (2006.01) |

(52) U.S. Cl.
CPC ...... *A61F 13/0276* (2013.01); *A61F 13/0253* (2013.01); *A61F 13/0273* (2013.01); *A61F 13/08* (2013.01); *A61F 13/105* (2013.01); *A61F 13/107* (2013.01); *A61L 24/04* (2013.01); *C09J 7/21* (2018.01); *A61F 2013/00119* (2013.01); *C09J 201/00* (2013.01); *C09J 2205/114* (2013.01); *C09J 2400/263* (2013.01); *C09J 2407/00* (2013.01); *C09J 2425/00* (2013.01); *C09J 2471/006* (2013.01); *C09J 2475/006* (2013.01); *C09J 2499/006* (2013.01)

(58) Field of Classification Search
CPC .. A61F 13/0276; A61F 13/0273; A61F 13/08; A61F 13/105; A61F 13/107; A61F 13/0253; A61F 2013/00119; C09J 7/21; C09J 2407/00; C09J 2425/00; C09J 2205/114; C09J 2499/006; C09J 2471/006; C09J 201/00; C09J 2400/263; C09J 2475/006; A61L 24/04
See application file for complete search history.

(56) References Cited

U.S. PATENT DOCUMENTS

| | | | | |
|---|---|---|---|---|
| 4,034,751 A | * | 7/1977 | Hung ............... | A61F 13/00017 156/155 |
| 4,414,970 A | * | 11/1983 | Berry ............... | A61F 13/00038 602/75 |
| RE31,886 E | * | 5/1985 | Hodgson ............ | A61F 13/023 128/849 |
| 4,699,133 A | * | 10/1987 | Schafer ............ | A61F 13/00987 427/208.6 |
| 4,944,958 A | * | 7/1990 | Langen ............. | A61F 13/0273 427/2.31 |
| 6,267,744 B1 | * | 7/2001 | Roberts ............ | D03D 15/08 605/44 |
| 7,960,603 B2 | * | 6/2011 | Evans .............. | A61F 13/04 428/216 |
| 8,021,347 B2 | * | 9/2011 | Vitaris ............ | A61F 13/00068 602/52 |
| 8,403,873 B2 | * | 3/2013 | Schuren ............ | A61F 13/069 602/53 |

* cited by examiner

*Primary Examiner* — Kevin R Kruer

(57) ABSTRACT

An adhesive elastomeric tape comprising 90 grade cheesecloth that is knitted with a medium gauge elastic yarn through a stitch bonding machine. The cloth is then coated with a petroleum base adhesive using a unique strike through method that allows a adhesive to pass through while coating both sides. A style of athletic tape that is flexible, durable, and adhesive simultaneously.

1 Claim, 2 Drawing Sheets

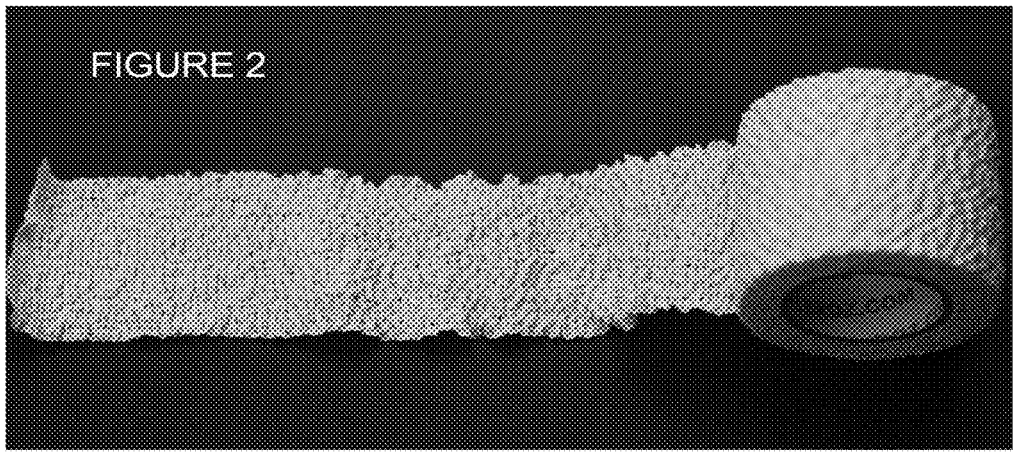

ABG STRETCH TAPE

BACKGROUND OF INVENTION

Figure 1:
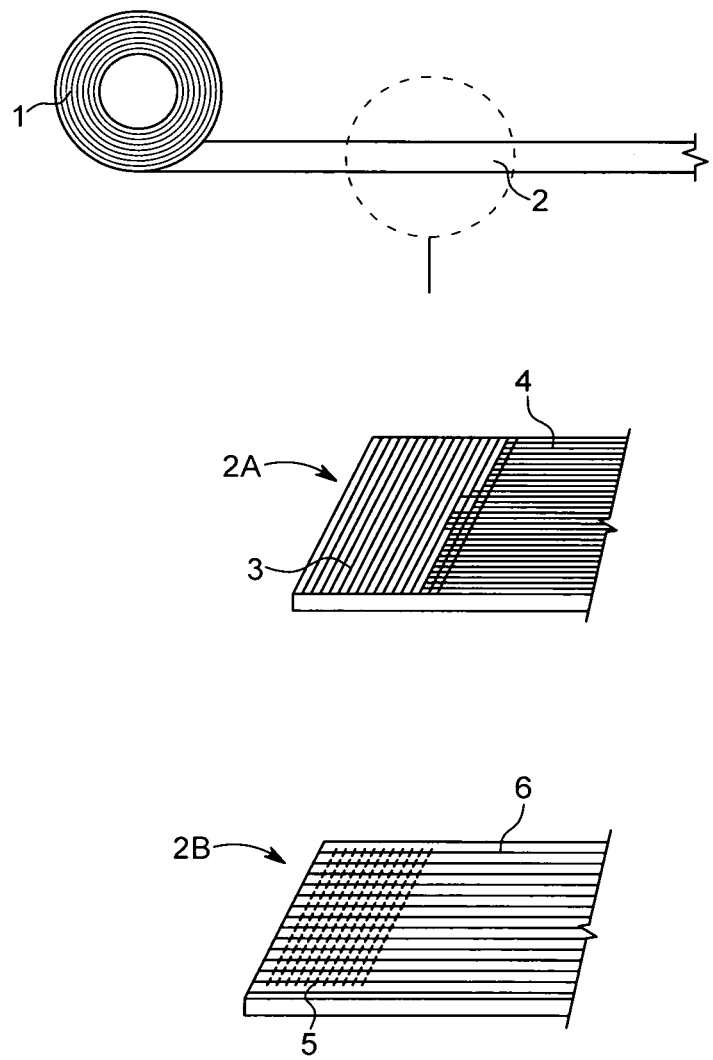

The present invention is in the technical field of sports and athletic equipment. More particularly, the present invention is in the technical field of athletic tape. Current tapes on the market either lack flexibility, durability, or adhesiveness; never incorporating all three. The most common athletic tape is 100% cloth and used for many purposes within the sporting world, such as wrapping a hockey stick or holding fingers together. While standard athletic tape can protect skin its use in weightlifting and other sports it is not ideal. While using a weighted barbell, standard athletic tape's lack of flexibility commonly causes bruising and swelling on the skin under the tape. Other tapes that use a combination of cotton and polyester provide decent durability and flexibility but lack strong adhesive, causing the tape to unravel and fail its intended use.

SUMMARY OF THE INVENTION

The present invention is an athletic tape designed to be adhesive, flexible, and durable simultaneously; allowing athletes to achieve optimal performance. This specific athletic tape is ideal for wrapping the thumb to improve the hook grip in weightlifting, wrapping forearms to protect from atlas stones in strongman competitions, covering shins to prevent barbell cuts and wrapping the entire palm of hand to protect a torn callus which is common amongst athletes. Other common uses include wrapping baseball bats and tennis rackets for grip, taping fingers for golf, wrapping wrists during judo, fingers for fishermen and ankles for ice skaters.

BRIEF DESCRIPTION OF THE IMAGE

FIG. 1. Is a perspective sketch of the athletic tape 1, the present invention, illustrating a cross section of the final product as it comes off the roll 2. The orientation of the cheesecloth "fabric weave" 2A including 36 threads per transverse inch 3, 44 threads per longitudinal inch 4, and the addition of the elastic yarn "elastic stitching." 2B comprising eight stitches per transverse inch 5 and twelve threads per longitudinal inch 6

FIG. 2. Is a perspective image of the athletic tape of the present invention in the same format as the sketch in FIG. 1.

DETAILED DESCRIPTION OF THE INVENTION

Referring now to the invention in more detail, FIGS. 1 and 2 show athletic tape that was manufactured by feeding 90 grade cheesecloth into a stitch bonding machine that knits in the elastic yarn. The stitching is designed to allow stretch along the length, but none along the width. Weaving this specific number of threads of elastic into the highest grade cheesecloth provides comfort, flexibility and durability.

Adhesive is then applied using a knife-over-roll coating technique to attain a "strike through" effect. This unique coating provides adhesive on both sides of the tape. The coating is applied with the fabric stretched fully extended and then immediately relaxed prior to entering the heated drying ovens to allow the tape to maintain its high stretch capabilities.

The finished product is extremely flexible, easily hand tearable, very adhesive and durable. These combined qualities make this tape unique in the industry.

The invention claimed is:
1. A method of making an adhesive tape comprising:
   supplying a base fabric material composed of grade#90 cheesecloth comprising 100% cotton fabric and a 44×36 thread count per inch;
   operating a stitch bonding machine to knit into said base fabric 12 elastic 105 denier threads per inch in the traverse direction and 8 elastic 105 denier threads per inch in the longitudinal direction;
   fully extending the base fabric;
   operating a knife-over-roll coating machine to apply an adhesive over the entire surface of said extended base fabric wherein said adhesive comprises a rubber blend with a viscosity of 300,000-500,000 cps and wherein said rubber blend comprises 68-74% solids of natural rubber and styrene-isoprene-styrene in a solvent comprising heptane and toluene;
   relaxing the adhesive coated base fabric; and
   drying the adhesive coated base fabric in a drying oven.

* * * * *